United States Patent [19]

Jasys

[11] Patent Number: 4,462,934

[45] Date of Patent: Jul. 31, 1984

[54] BIS-ESTERS OF DICARBOXYLIC ACIDS WITH AMOXICILLIN AND CERTAIN HYDROXYMETHYLPENICILLANATE 1,1-DIOXIDES

[75] Inventor: Vytautas J. Jasys, New London, Conn.

[73] Assignee: Pfizer Inc., New York, N.Y.

[21] Appl. No.: 481,108

[22] Filed: Mar. 31, 1983

[51] Int. Cl.$^3$ .......................................... C07D 499/48
[52] U.S. Cl. .................................. 260/239.1; 424/271
[58] Field of Search ...................... 260/239.1; 424/271

[56] References Cited

U.S. PATENT DOCUMENTS

| | | | |
|---|---|---|---|
| 4,234,579 | 11/1980 | Barth | 424/246 |
| 4,244,951 | 1/1981 | Bigham | 424/250 |
| 4,342,768 | 8/1982 | Kellogg | 424/250 |
| 4,342,772 | 8/1982 | Godtfredsen | 424/271 |
| 4,377,590 | 3/1983 | Myers | 424/271 |

FOREIGN PATENT DOCUMENTS 2044255 10/1980 United Kingdom .

*Primary Examiner*—Natalie Trousof
*Assistant Examiner*—Vera C. Clarke
*Attorney, Agent, or Firm*—Charles J. Knuth; Albert E. Frost; Peter C. Richardson

[57] ABSTRACT

Antibacterial bis-esters of 1,4-cyclohexanedicarboxylic acids and alkane dicarboxylic acids wherein the ester moieties are derived from different alcohols; one alcohol being hydroxymethylpenicillanate 1,1-dioxide, or the 6-beta-hydroxymethyl or the 6-alpha-aminomethyl derivative thereof; and the other being 6-[D-(2-amino-2-(p-hydroxyphenyl)acetamido)]penicillanic acid (amoxicillin); and pharmaceutically acceptable salts thereof; a method for the use of said esters and their salts, and methods for their preparation.

13 Claims, No Drawings

BIS-ESTERS OF DICARBOXYLIC ACIDS WITH AMOXICILLIN AND CERTAIN HYDROXYMETHYLPENICILLANATE 1,1-DIOXIDES

BACKGROUND OF THE INVENTION

Efforts to develop beta-lactam antibiotics, i.e., penicillins and cephalosporins, having improved efficacy, particularly against gram-negative and beta-lactam resistant organisms, have progressed along several paths. The first is directed to chemical modification of the substituent groups on the basic penam or cepham nucleus, especially of the amino groups at the 6- and 7-positions, respectively, of said nuclei. A second path is aimed at modification of the basic beta-lactam nuclei of said antibiotics. More recently, attention has focused on physical and chemical combinations of a beta-lactam antibiotic with a beta-lactamase inhibitor; i.e., a substance which inhibits beta-lactamases and, as a result, prevents their degrading the beta-lactam ring of said antibiotics to products devoid of antibacterial activity.

Penicillanic acid 1,1-dioxide and esters thereof readily hydrolyzable in vivo and useful as antibacterial agents and beta-lactamase inhibitors are disclosed in U.S. Pat. No. 4,234,579, issued Nov. 18, 1980.

Bis-esters of alkanediols with penicillins and penicillanic acid 1,1-dioxide useful, because of their tendency to hydrolyze in vivo to provide both a penicillin and a beta-lactamase inhibitor, as antibacterial agents against beta-lactamase producing bacteria are described in U.S. Pat. No. 4,244,951, issued Jan. 13, 1981, and in British Pat. Application 2,044,255A, published Oct. 15, 1980. U.S. Pat. No. 4,364,957, issued Dec. 21, 1982 describes bis-esters of alkanediols with 6-acyl amidopenicillanic acid and 2-beta-acetoxymethyl-2-alpha-methyl-(5R)penam-3-alpha-carboxylic acid 1,1-dioxide as antibacterial agents. In U.S. Pat. No. 4,342,772 issued Aug. 3, 1982, analogous compounds are disclosed in which penicillins and beta-lactamase inhibitors such as penicillanic acid 1,1-dioxide, clavulanic acid and 6-beta-halopenicillanic acids are linked via 1,1-alkanediol groups.

In copending application Ser. No. 407,540, filed Aug. 12, 1982 and assigned to the same assignee, there are described bis-esters of methanediol in which one hydroxy group is esterified with the carboxy group of a beta-lactamase inhibitor and the other with the carboxy group of an O-acyl derivative of amoxicillin.

Bis-esters of 1,1-alkanediols with 6-beta-hydroxymethylpenicillanic acid 1,1-dioxide are disclosed in U.S. Pat. No. 4,342,768. The corresponding derivatives of 6-alpha-hydroxymethylpenicillanic acid 1,1-dioxide are disclosed in copending application Ser. No. 338,794, filed Jan. 11, 1982, assigned to the same assignee. 6-Aminoalkyl penicillanic acid 1,1-dioxide beta-lactamase inhibitors are disclosed in copending application Ser. No. 434,731, filed Oct. 21, 1982 and assigned to the same assignee.

U.S. Pat. No. 4,377,590, issued Mar. 22, 1983 describes derivatives of methanediol with a betalactamase inhibitor, e.g. sulbactam or its 6-hydroxymethyl derivative, and amoxicillin, the latter being linked through its phenolic group. Amoxicillin, 6-[D-(2-amino-2-[p-hydroxyphenyl]acetamido)]penicillanic acid is known from U.S. Pat. No. 3,192,198 and 28,744. p-Acyl derivatives of amoxicillin are disclosed in U.S. Pat. Nos. 2,985,648, and 3,520,876.

SUMMARY OF THE INVENTION

This invention relates to a new type of bis-ester antibacterial agent derived from a beta-lactamase inhibitor and a penicillin. More particularly it relates to bis-esters of 1,4-cyclohexanedicarboxylic acid and alkane dicarboxylic acids wherein the ester moieties are derived from two different alcohols, one alcohol being hydroxymethyl penicillanate 1,1-dioxide, or the 6-beta-hydroxymethyl or the 6-alpha-aminomethyl derivative thereof; and the other being 6-[D-(2-amino-2-(p-hydroxyphenyl)acetamido)]penicillanic acid. The compounds have formula I:

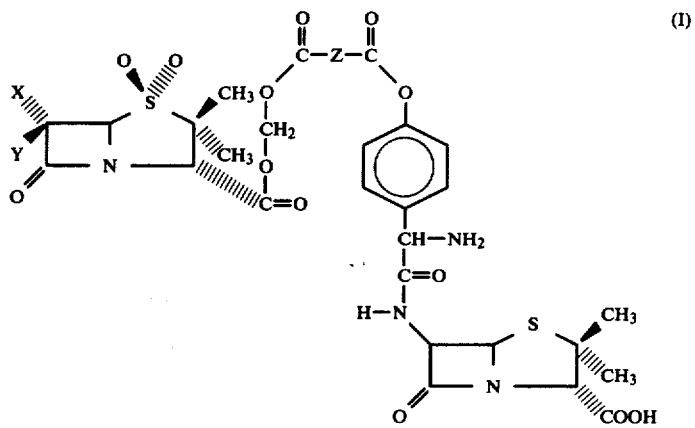

wherein
Z is 1,4-cyclohexylene or alkylene having from 1 to 6 carbon atoms; and

Also embodied in this invention are the pharmaceutically acceptable salts of formula I compounds, compounds of formula I wherein the amino group of the amoxicillin residue is protected by means of a 1-methyl-2-methoxycarbonylvinyl, a benzyloxycarbonyl or a 4-nitrobenzyloxycarbonyl group; and formula I compounds wherein X is aminomethyl wherein the amino group is protected by one of said groups and especially by benzyloxycarbonyl or 4-nitrobenzyloxycarbonyl.

3

Favored compounds of formula I are those wherein Z is trans-1,4-cyclohexylene, or alkylene having from 3 to 4 carbon atoms.

When depicting compounds of structure I, the bicyclic ring system is understood to substantially be in the plane of the paper. Broken line attachment of a group to said ring system indicates that the group is attached from below the plane of the paper, and such a group is said to be in the alpha-configuration. Conversely, wedge line attachment of a group to the ring system indicates that the group is attached from above the plane of the paper, and this latter configuration is referred to as the beta-configuration.

DETAILED DESCRIPTION OF THE INVENTION

The compounds of formula I are prepared by methods known in the art for the synthesis of esters. Critical review of formula I indicates the overall formula can be dissected into several groups (or fragments) or combinations of groups. This exercise, of course, affords basis for the several processes by which formula I compounds can be prepared. Dissection of formula I on the basis of its simple component groups is shown below:

4

R is OH, Cl, Br, O—CO—($C_{1-4}$)alkoxy, O-alkali metal or O-CO—($C_{1-4}$)alkyl; but is preferably chloro;

X, Y and Z are as defined above;

is coupled under standard conditions with amoxicillin, the amino group of which is protected by a group easily removable under conditions which affect substantially only the protecting group. Representative of such groups are 1-methyl-2-methoxycarbonylvinyl, benzyloxycarbonyl and 4-nitrobenzyloxycarbonyl.

Because of their ease of preparation and general reactivity, the preferred compounds of formula II are those wherein R is Cl. They are readily prepared by reacting the formula II compound wherein R is OH with a halogenating agent, especially with oxalyl chloride, in a reaction-inert solvent at about 0° C. A tertiary amine such as pyridine, triethylamine, dimethylaminopyridine, diisopropylethylamine, is desirably added as acid acceptor. Suitable solvents for this reaction are methylene chloride, chloroform, benzene, toluene, tetrahydrofuran, dioxane and dimethylformamide.

The acid chloride thus produced is then coupled with amoxicillin, the amino group of which is protected by one of the protecting groups previously mentioned. Additionally, the carboxy group of said amoxicillin is

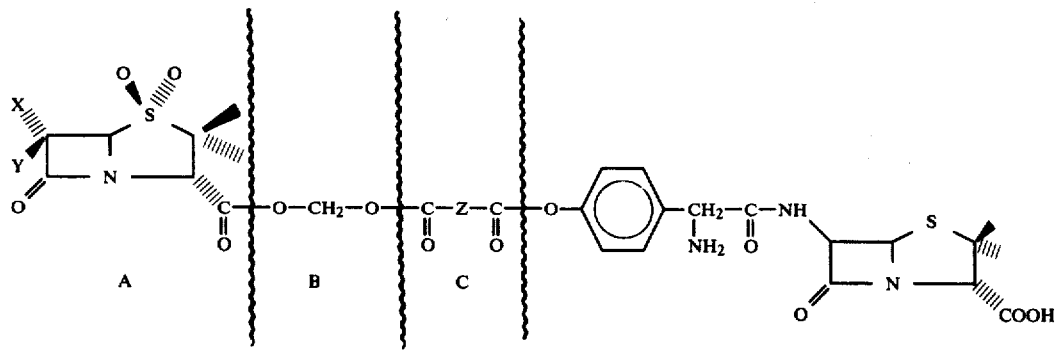

Thus, the four principal fragments, suggest the following processes. In the abbreviated reactions presented below, wherein the above-indicated fragments represent the reactants, it is understood that a reactive form of said fragment is intended. For example, in reaction (a), the acid chloride of fragment A-B-C and the alcoholic (phenolic) form of fragment D would be used as reactants in the presence of an acid acceptor.

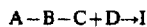 (a)

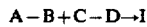 (b)

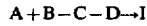 (c)

Method (a), the reaction of a reactive form of fragment A-B-C with an active form of fragment D is the favored method for making formula I compounds. In said method fragment A-B-C in the form of a reactive derivative (II)

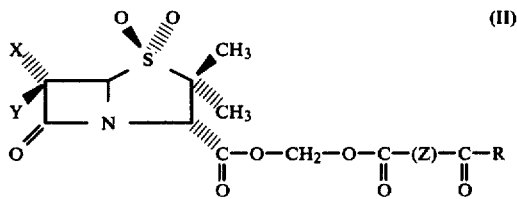

wherein transformed to a salt group with a quaternary amine in order to achieve a reactant soluble in the reaction medium. Typical of such salts are the lower alkyl ammonium salts and especially the tetrabutyl-ammonium salt. The coupling reaction is carried out in a reaction-inert solvent such as those mentioned above at ambient temperature, and in the presence of a tertiary amine such as dimethylaminopyridine.

The product of this coupling reaction, a formula I compound, the amino group of which is protected, can be recovered as such and the protecting group subsequently removed. However, when the protecting group is 1-methyl-2-methoxycarbonylvinyl, said group is easily removed by treating the product with aqueous acid, e.g. aqueous HCl or other mineral acid. For this reason, the 1-methyl-2-methoxycarbonylvinyl is the preferred amino protecting group.

When benzyloxycarbonyl or 4-nitrobenzyloxycarbonyl are used as protecting groups, the coupling product is recovered and then subjected to catalytic hydrogenolysis in a reaction-inert solvent at from about 0° to 60° C. over a noble metal catalyst at from about 1-10 atmospheres. Representative solvents are ($C_{1-4}$)alkanols, cyclic ethers (e.g. dioxane, tetrahydrofuran), chlorinated hydrocarbons (e.g. methylene chloride, chloroform), low molecular weight esters (e.g. ethyl and n-butyl acetate), water, and mixtures thereof, and preferably a 1:1 mixture of methylene chloride:isopropanol. A supported noble metal catalyst is generally favored over a non-supported one since it permits better distribution of catalyst in the reaction mixture. Palladium/carbon and rhodium/carbon, favored catalysts, are normally used at about 0.5 to 5.0 times the weight of the product to be hydrogenolyzed.

In formula II compounds, when X is aminomethyl ($H_2NCH_2$), the favored procedure for converting them to formula I compounds wherein X has the same meaning is to first protect the amino group, preferably as the benzyloxycarbonyl or 4-nitrobenzyloxycarbonyl derivative, prior to subjecting it to the above described coupling reaction. Upon completion of said reaction, the protecting group is removed by catalytic hydrogenolysis as described above.

The required reactive derivative of the A-B-C containing fragment is conveniently produced by reacting a cationic salt of fragment A and a compound of formula $R_1$—$CH_2$—$R_2$ wherein $R_1$ and $R_2$ are good leaving groups, e.g., chloro, bromo, iodo, alkylsulfonyloxy, benzenesulfonyloxy or toluenesulfonyloxy, said compound generally being used in excess, e.g. a four-fold excess. Representative cationic (M) salts of fragment A are alkali metal salts, such as sodium and potassium salts; alkaline earth metal salts, such as calcium and barium salts; and amine salts, such as trimethylamine, triethylamine, tributylamine, diisopropylethylamine, tetra($C_{1-4}$)alkyl ammonium, N-methylmorpholine, N-methylpiperidine, N-methylpyrrolidine, N,N'-dimethylpiperazine, 1,2,3,4-tetrahydroquinoline, cyclohexylamine, benzylamine, morpholine and other amines used to form salts with penicillins. In practice $R_2$ is $R_1$ or a better leaving group than $R_1$, e.g. when $R_1$ is chloro, $R_2$ is bromo or iodo.

The reaction

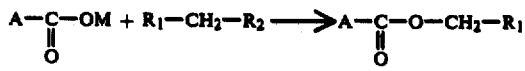

is usually carried out by contacting the reagents in a polar, organic solvent, at a temperature in the range from about 0° C. to about 80° C., and preferably from 25° to 50° C., usually in substantially equimolar proportions, although an excess of either reagent, for example up to a ten-fold excess, can be used. A wide variety of solvents can be used, but it is usually advantageous to use a relatively polar solvent, since this has the effect of speeding up the reaction. Typical solvents include N,N-dimethylformamide, N,N-dimethylacetamide, N-methylpyrrolidone, dimethylsulfoxide and hexamethylphosphoramide. The reaction time varies according to a number of factors, but at about 25° C. reaction times of several hours, e.g. 12 to 24 hours, are commonly used. When $R_1$ is chloro or bromo, it is sometimes advantageous to add up to about one molar equivalent of an alkali metal iodide, which has the effect of speeding up the reaction. When $R_1$ is chloro and $R_2$ is bromo or iodo, it is preferred to carry out the reaction in excess of reactant $R_1$—$CH_2$—$R_2$.

The A-B containing fragment thus produced is then reacted with a reactive derivative of the C fragment, e.g. a cationic salt thereof:

-continued

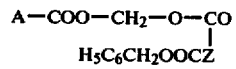

wherein $R_2$, M and Z are as defined above.

The C-containing fragment is protected in the form of an easily removed ester group, e.g. benzyl, to minimize side reactions. Selective removal of the benzyl group by catalytic hydrogenolysis under conditions described above affords the corresponding acid. It is then converted to the acid chloride as described above for reaction with amoxicillin, the amino group of which is protected, as is described above.

The compounds of the formula (I) will form acid addition salts as noted above. Said acid addition salts are prepared by standard methods for making salts of amino containing penicillin compounds, for example by combining a solution of the compound of formula (I) in a suitable solvent (e.g. water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate, benzenesulfonate, 4-chlorobenzenesulfonate, 4-toluenesulfonate and 2-naphthylenesulfonate salts. Formula I compounds wherein X is $H_2N$—$CH_2$— can form mono- or diacid salts as those skilled in the art will recognize, depending upon the amount of acid used.

The free carboxy group of formula I allows formation of cationic salts of the type enumerated above. Said salts are prepared as described above for acid addition salts, but, of course, using the appropriate base in place of an acid.

The compounds of formula I, and the salts thereof, can be purified by conventional methods for penicillin compounds, e.g. recrystallization or chromatography, but due regard must be given to the lability of the beta-lactam ring systems and the ester linkages.

When contemplating therapeutic use for a salt of an antibacterial compound of this invention, it is, of course, necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

Similarly, the known beta-lactamase inhibitors 2-beta-acetoxymethylpenicillanic acid 1,1-dioxide and 2-beta-chloromethylpenicillanic acid 1,1-dioxide can be used in place of the above-mentioned beta-lactamase inhibitors to produce related antibacterial bis-esters by the reactions described herein. Said bis-esters are used in the same manner as are the compounds of formula I.

The compounds of formula I, as well as their salts, possess in vivo antibacterial activity in mammals. This activity can be demonstrated by standard techniques for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and have also received a formula I compound. The compounds of formula I, as well as their salts, can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

Formula I compounds break down to 6-(2-amino-2-[4-hydroxyphenyl]acetamido)penicillanic acid (amoxicillin) and the corresponding penicillanic acid 1,1-dioxide derivatives (e.g. sulbactam when each of X and Y is hydrogen; or to the corresponding 6-beta-hydroxymethyl or 6-alpha-aminomethyl derivative thereof) after administration to a mammalian subject by both the oral and parenteral route. Sulbactam (or the other compounds above) then functions as a beta-lactamase inhibitor, and it increases the antibacterial effectiveness of the amoxicillin. Thus, compounds of formula I will find use in the control of bacteria which are susceptible to an approximately equimolar mixture of amoxicillin and a beta-lactamase inhibitor, for example a 1:1 mixture of amoxicillin and sulbactam for the compound wherein each of X and Y is hydrogen. Examples of such bacteria are susceptible strains of *Escherichia coli* and *Staphylococcus aureus*.

In determining whether a particular strain of *Escherichia coli* or *Staphylococcus aureus* is sensitive to a particular therapeutic compound or mixture, the in vivo test described earlier can be used. Alternatively, e.g., the minimum inhibitory concentration (MIC) of a 1:1 mixture of amoxicillin and beta-lactamase inhibitor, e.g. sulbactam, can be measured. The MIC's can be measured by the procedure recommended by the International Collaborative Study on Antibiotic Sensitivity Testing (Ericcson and Sherris, *Acta. Pathologica et Microbiologia Scandinav*, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The antibacterial compounds of this invention will normally be used orally at dosages in the range from 20 to about 100 mg per kilogram of body weight per day, and parenterally at dosages from about 10 to about 100 mg per kilogram of body weight per day, usually in divided doses. In some instances it may be necessary to use doses outside these ranges.

The following examples and preparations are provided solely for further illustration. Proton nuclear magnetic resonance spectra (pnmr) were measured for solutions in deuterated dimethyl sulfoxide (DMSO-d$_6$), and peak positions are reported in parts per million downfield from tetramethylsilane. The following abbreviations for peak shapes are used: bs, broad singlet; s, singlet; d, doublet; t, triplet; q, quartet, m, multiplet. In the Examples and Preparations no effort was made to optimize the yield of any given reaction.

EXAMPLE 1

6-[D-2-Amino-2-{p-(omega-(1,1-dioxopenicillanoyloxymethoxycarbonylbutyryloxy)phenyl}acetamido]-penicillanic Acid To a mixture of 50 ml methylene chloride, 4.09 g (0.010 mole) of 1,1-dioxopenicillanoyloxymethyl adipate hydrate, 0.88 ml (0.01 mole) pyridine and 1.73 ml (0.01 mole) diisopropylethylamine at 0° C. was added 0.96 ml (0.011 mole) of oxalyl chloride. The mixture was stirred at 0° C. for 20 minutes then concentrated under reduced pressure to about 15 ml volume. The concentrate was added to a suspension of 7.09 g (0.011 mole) of 6-[D-(2-(1-methyl-2-methoxycarbonylvinylamino)-2-(p-hydroxyphenyl)acetamido)]-penicillanic acid tetra-n-butyl ammonium salt and 1.22 g (0.011 mole) of dimethylaminopyridine in 50 ml of dimethylformamide. The resulting clear solution was stirred for 45 minutes then diluted with methylene chloride to 300 ml volume. The diluted solution was washed with 3×150 ml water and 1×200 ml brine (the emulsion which formed was broken by addition of water). The methylene chloride layer was dried ($Na_2SO_4$) then concentrated in vacuo to a viscous yellow oil (8.0 g).

The oil was taken up in 50 ml acetone, 20 ml of water added and the pH was adjusted to 1.5 with 1 N HCl. The solution was stirred for a half hour then stripped of acetone in vacuo.

Twenty five ml (half) of the aqueous residue was chromatographed on 250 g Sephadex LH-20 (Pharmacia Zinc Chemicals Inc., Piscataway, N.J., U.S.A.) using water as eluting agent. Fractions of 25 ml each were then taken every 2.5 minutes. Progress of the separation was monitored by thin layer chromatography (6:1 acetone:0.2 M sodium acetate), the chromatograms being developed by means of ammonia vapor and a spray of potassium permanganate solution (1.0 g $KMnO_4$, 2.0 g $K_2CO_3$, 200 ml $H_2O$). Fractions 30 and 31, thus found to contain the desired product, were combined and freeze dried to give 26 mg of solid. Fractions 26–29 comprising product and the amoxicillin reactant were combined, freeze dried, then redissolved in water (20 ml) and rechromatographed as before. Fractions 27 and 28 afforded 15 mg of desired product.

pnmr/DMSO-$d_6$/delta (ppm): 1.34 (s, 3H); 1.43 (s, 3H); 1.46 (s, 3H); 1.5 (s, 3H); 1.55–1.75 (bs, 4H), 2.4–2.7 (m, 4H); 3.27 (dd, 1H); 3.7 (dd, 1H); 4.14 (s, 1H); 4.55 (s, 1H); 4.82 (s, 1H); 5.2 (m, 1H); 5.4 (d, 1H); 5.45–5.5 (m, 1H); 5.83 (dd, 2H); 7.13 (d, 2H); 7.49 (d, 2H); 8.95–9.15 (bs, 1H).

EXAMPLE 2

The compounds listed below are prepared according to the procedure of Example 1 but using the mono 1,1-dioxopenicillanoyloxymethyl ester, or 6-substituted derivative thereof, of the appropriate alkane dicarboxylic acid or 1,4-cyclohexane dicarboxylic acid.

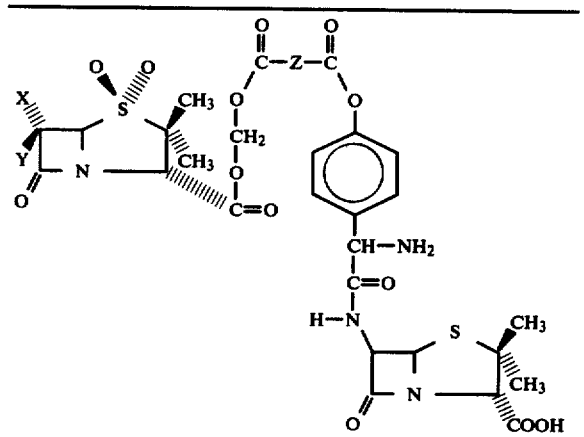

| X | Y | Z |
|---|---|---|
| H | H | —$CH_2$— |
| H | H | —$CH_2$—$CH_2$— |
| H | H | —$CH_2$—$CH_2$—$CH_2$— |
| H | H | —$(CH_2)_6$— |
| H | H | —$CH(CH_3)$— |
| H | H | —$C(C_2H_5)_2$— |
| H | H | —$CH_2$—$CH(CH_3)$—$CH_2$— |
| H | H | trans-1,4,-$C_6H_{10}$* |
| H | H | cis-1,4-$C_6H_{10}$* |
| H | $HOCH_2$ | —$CH_2$— |
| H | $HOCH_2$ | —$CH_2$—$CH_2$—$CH_2$— |
| H | $HOCH_2$ | —$(CH_2)_4$— |
| H | $HOCH_2$ | —$CH(i-C_3H_7)$— |
| H | $HOCH_2$ | —$CH_2$—$C(CH_3)_2$—$CH_2$— |
| H | $HOCH_2$ | trans-1,4-$C_6H_{10}$ |

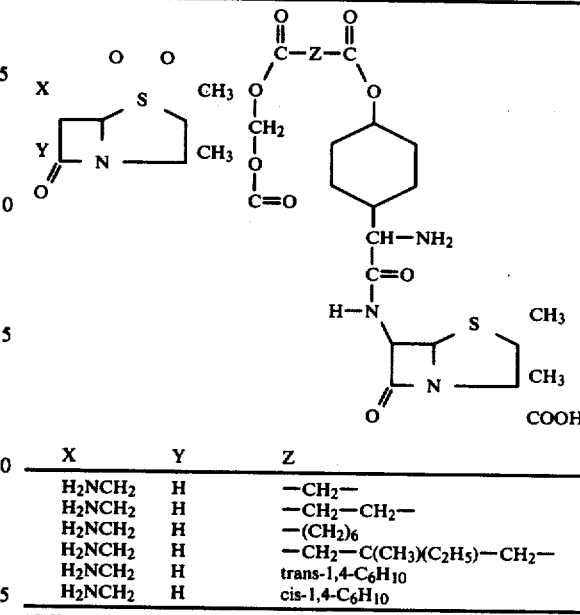

| X | Y | Z |
|---|---|---|
| $H_2NCH_2$ | H | —$CH_2$— |
| $H_2NCH_2$ | H | —$CH_2$—$CH_2$— |
| $H_2NCH_2$ | H | —$(CH_2)_6$ |
| $H_2NCH_2$ | H | —$CH_2$—$C(CH_3)(C_2H_5)$—$CH_2$— |
| $H_2NCH_2$ | H | trans-1,4-$C_6H_{10}$ |
| $H_2NCH_2$ | H | cis-1,4-$C_6H_{10}$ |

*$C_6H_{10}$ = cyclohexylene

PREPARATION A

Monobenzyl Esters of Dicarboxylic Acids
trans-1,4-Cyclohexanedicarboxylic acid monobenzyl ester To a solution of 1.0 g (2.8 mmole) dibenzyl trans-1,4-cyclohexanedicarboxylate in 20 ml tert-butanol (warm) is added a solution of 1.9 g potassium hydroxide in 10 ml tert-butanol. After stirring at room temperature overnight the cloudy mixture is evaporated to remove solvent, taken up in water and acidified to pH 5.3; then, after 30 minutes, acidified to pH 5.25 with dilute hydrochloric acid. The precipitated solid is collected on a filter, redissolved in dilute sodium bicarbonate solution and this readjusted to pH 5.25 to precipitate the purified monoester $^1H$—NMR (DMSO-$d_6$) ppm (delta): 1.1–2.3 (m, 10H), 5.1 (s, 1H), 7.35 (s, 5H).

The monobenzyl esters of the following dicarboxylic acids are obtained in like manner by the above procedure:

n-butylmalonic acid
methylmalonic acid
ethylmalonic acid
isopropylmalonic acid
diethylmalonic acid
adipic acid
3-methylglutaric acid
3-ethylglutaric acid
3-ethyl-3-methylglutaric acid
2-methylglutaric acid
2,2-dimethylglutaric acid
2-methylsuccinic acid
3-methyladipic acid
cis-1,4-cyclohexane dicarboxylic acid.

PREPARATION B

Cis-1,2-cyclohexanedicarboxylic acid monobenzyl ester

To 15.4 g (0.10 mole) cis-1,2-cyclohexanedicarboxylic anhydride in 200 ml toluene is added dropwise a solution of 10.8 g (0.10 mole) benzyl alcohol in 50 ml of toluene. The mixture is stirred at room temperature for one hour then warmed to 60° C. and held at this temperature for one hour. The solvent is evaporated to a small volume and the product monoester obtained upon cooling and filtration of the precipitated solid.

Alternatively, the reaction mixture in toluene is treated with an equimolar amount of ethanolic potassium hydroxide to obtain the potassium salt of the monobenzyl ester. The sodium salt is obtained by use of methanolic sodium hydroxide in like manner.

The corresponding monobenzyl esters or their sodium or potassium salts are obtained from the following dicarboxylic acid anhydrides by the above procedure:
succinic anhydride
glutaric anhydride (refluxed in toluene overnight).

PREPARATION C

Benzyl 1,1-dioxopenicillanoyloxymethyl succinate

To a mixture of 9.2 g (0.044 mole) benzyl succinate half ester in 200 ml of chloroform and 25 ml water was added 40% aqueous tetrabutylammonium hydroxide with vigorous stirring until a pH of 8.5 was obtained. The chloroform layer was separated and the aqueous layer extract (1×100 ml) with chloroform. The combined chloroform extracts were dried (Na$_2$SO$_4$) and concentrated in vacuo to an oil. The oil was combined with 200 ml toluene and 16.5 g (0.044 mole) iodomethyl penicillanate 1,1-dioxide was added. The mixture was stirred 30 minutes, diluted to 400 ml with ethyl acetate and the precipitated tetrabutylammonium iodide removed by filtration. The filter cake was washed with 100 ml ethyl acetate and the combined filtrates were washed with saturated NaHCO$_3$(1×100 ml), water (1×100 ml), brine (1×100 ml), dried (Na$_2$SO$_4$) and concentrated in vacuo to an oil. Chromatography on silica gel (1 kg), eluting with 1:1 (v/v) ethyl acetate/hexane), gave 8.5 g (43%) of a white solid.

$^1$H—NMR (CDCl$_3$) ppm (delta): 1.45 (s, 3H), 1.63 (s, 3H), 2.77 (s, 4H), 3.47 (d, 2H), 4.43 (s, 1H), 4.62 (t, 1H), 5.17 (s, 2H), 5.84 (AB quartet, 2H), 7.4 (s, 5H).

In the same manner the following compounds were also prepared from the appropriate monobenzyl ester:

Benzyl 1,1-dioxopenicillanoyloxymethyl glutarate-(61% yield)-$^1$H—NMR (CDCl$_3$) ppm (delta): 1.42 (s, 3H), 1.6 (s, 3H), 1.8-2.2 (m, 2H), 2.28-2.68 (m, 4H), 3.45 (d, 2H), 4.4 (s, 1H), 4.6 (t, 1H), 5.14 (s, 1H), 5.8 (AB quartet, 2H), 7.37 (s, 5H).

Benzyl 1,1-dioxopenicillanoyloxymethyl adipate-(47% yield)-$^1$H—NMR (CDCl$_3$) ppm (delta): 1.46 (s, 3H), 1.63 (s, 3H), 1.53-1.86 (m, 4H), 2.22-2.6 (m, 4H), 3.46 (d, 2H), 4.42 (s, 1H), 4.6 (t, 1H), 5.13 (s, 2H), 5.82 (AB quartet, 2H), 7.33 (s, 5H).

Benzyl 1,1-dioxopenicillanoyloxymethyl dimethylmalonate-(73.8% yield)-$^1$H—NMR (CDCl$_3$) ppm (delta): 1.4 (s, 3H), 1.53 (s, 9H), 3.45 (d, 2H), 4.4 (s, 1H), 4.56 (t, 1H), 5.22 (s, 2H), 5.78 (AB quartet, 2H), 7.35 (s, 5H).

Benzyl 1,1-dioxopenicillanoyloxymethyl malonate-(45% yield)-$^1$H—NMR (CDCl$_3$) ppm (delta): 1.43 (s, 3H), 1.6 (s, 3H), 3.46 (d, 2H), 3.53 (s, 2H), 4.42 (s, 1H), 4.6 (t, 1H), 5.2 (s, 2H), 5.85 (AB quartet, 2H), 7.39 (s, 5H); infrared spectrum (nujol) cm$^{-1}$: 1795, 1790.

In like manner the remaining monobenzyl esters provided in Preparations A and B are converted to the corresponding compounds of the formula

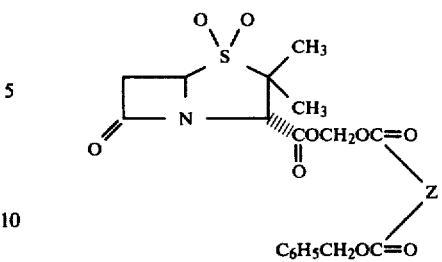

where Z is as defined for the starting monobenzyl ester.

Alternatively, the above benzyl, 1,1-dioxopenicillanoyloxymethyl diesters are prepared as described below for the adipate diester.

A mixture of 17.0 g (0.0665 mole) sodium 1,1-dioxopenicillanate, 18.0 g (0.0634 mole) benzyl chloromethyl adipate, 6.7 g (0.020 mole) tetrabutylammonium bromide and 300 ml acetone is heated under nitrogen at reflux overnight. The acetone is evaporated and the residual gel taken up in 300 ml ethyl acetate. Water (150 ml) is added, the organic layer is separated and the aqueous layer extracted with fresh ethyl acetate (150 ml). The combined organic extracts are washed with water (3×250 ml), brine (2×150 ml), dried (Na$_2$SO$_4$) and concentrated in vacuo to an oil (31.8 g). The oil is chromatographed on 700 g silica gel, eluting with 2:1 hexane/ethyl acetate to remove the less polar impurities, then with 1:1 ethyl acetate/hexane to remove the product. Evaporation of solvent from the product fractions affords 27.3 g (89.5%).

PREPARATION D

Sodium 1,1-Dioxopenicillanoyloxymethyl Succinate

A solution of 8.4 g (0.019 mole) of benzyl 1,1-dioxopenicillanoyloxymethyl succinate in 75 ml of tetrahydrofuran was added to a suspension of 4 g of 10% (w/w) palladium on carbon in tetrahydrofuran (THF) and shaken under 50 psi (3.52 kg/cm$^2$) of hydrogen on an hydrogenation apparatus. After 30 minutes the catalyst was removed by filtration through a filter aid and the cake washed with 75 ml of THF, the combined filtrates were concentrated in vacuo and taken up in 75 ml of ethyl acetate. To this solution was added 3.07 g (0.019 mole) of sodium-2-ethylhexanoate with stirring. After 15 minutes the precipitate was filtered, washed with diethyl ether and dried under nitrogen to give 6.8 g (95%) of a white solid.

The following sodium salts were prepared in like manner, except that in cases where no precipitate forms upon addition of sodium 2-ethylhexanoate, ethyl ether is added to effect precipitation.

a. Sodium 1,1-dioxopenicillanoyloxymethyl glytarate-(93% yield)-$^1$H—NMR (D$_2$O) ppm (delta): 1.48 (s, 3H), 1.63 (s, 3H), 1.6-2.7 (m, 6H), 3.22-3.98 (m, 2H), 4.68 (s, 1H), 4.8-5.13 (m, 1H), 5.86 (AB quartet, 2H).

b. Sodium 1,1-dioxopenicillanoyloxymethyl adipate-(79% yield)-$^1$H—NMR (D$_2$O) ppm (delta): 1.46 (s, 3H), 1.63 (s, 3H), 1.44-1.8 (m, 4H), 2.1-2.6 (m, 4H), 3.1-3.96 (m, 2H), 4.56-4.76 (HOD peak, hides C-3H), 5.0-5.16 (m, 1H), 5.92 (AB quartet, 2H).

c. Sodium 1,1-dioxopenicillanoyloxymethyl dimethylmalonate-(94.5% yield)*-$^1$H—NMR (D$_2$O) ppm delta: 1.33 (s, 6H), 1.44 (s, 3H), 1.58 (s, 3H), 3.16-3.9 (m, 2H), 4.65 (s, 1H), 4.93-5.1 (m, 1H), 5.93 (AB quartet, 2H); infrared spectrum (nujol), 1780 cm$^{-1}$.

*Recrystallization from ethyl acetate/hexane affords crystalline needles.

d. Sodium 1,1-dioxopenicillanoyloxymethyl malonate-(88% yield)-¹H—NMR (D₂O) ppm (delta): 1.45 (s, 3H), 1.6 (s, 3H), 3.2–3.93 (m, 2H), 4.66 (s, 1H), 4.96–5.13 (m, 1H), 5.88 (AB quartet, 2H). It was noted that the CH₂-malonate hydrogen atoms exchanged with D₂O.

e. The remaining benzyl esters provided in Preparation C are hydrogenated and converted to the corresponding sodium salt by the above procedure. The corresponding potassium salt is obtained by use of potassium 2-ethyl hexanoate in the above procedure.

PREPARATION E

Crystalline 1,1-dioxopenicillanoyloxymethyl Adipic Acid Hydrate

To 400 ml acetone is added 48.5 g (0.19 mole) sodium, 1,1-dioxopenicillanate, 48.0 g (0.17 mole) benzyl chloromethyl adipate and 19.3 g (0.06) tetrabutylammonium bromide. The mixture is heated at reflux under nitrogen overnight, filtered, washed with acetone and the filtrate evaporated. The residue is taken up in 500 ml ethyl acetate, washed alternately with brine and water, 250 ml portions, brine again and dried (MgSO₄). Evaporation of solvent in vacuo afforded 89.6 g light yellow oil. The oil is taken up in 250 ml ethyl acetate, 20.0 g 10% Pd/C added and the mixture is hydrogenated at 3.52 kg/cm² for one hour. After adding 15 g of fresh catalyst the hydrogenation is continued for 2.5 hours. The catalyst is removed by filtration, the cake washed with acetone (1500 ml) and the combined filtrate and washings evaporated in vacuo to obtain a viscous oil. The oil is taken up in 150 ml acetone and water added slowly to start crystallization, then continued until 800 ml water is added. After stirring 30 minutes, the crystalline product is recovered by filtration, washing with water and air dried to obtain 58.2 g of the title carboxylic acid. Recrystallization from ethyl acetate affords the crystalline monohydrate, m.p. 100°–102° C.

Analysis: Calculated for C₁₅H₂₁O₉NS.H₂O: C, 44.00; H, 5.66; N, 3.42. Found: C, 43.93; H, 5.65; N, 3.42.

The crystallinity was verified by X-ray crystallography.

PREPARATION F

Sodium 1,1-Dioxopenicillanoyloxymethyl trans-1,4-cyclohexanedicarboxylate

A. Benzyl chloromethyl trans-1,4-cyclohexanedicarboxylate

To a mixture of 3.06 g (0.036 mole) sodium bicarbonate, 5.46 g (0.018 mole) potassium benzyl trans-1,4-cyclohexanedicarboxylate, 50 ml water and 500 ml chloroform is added 6.17 g (0.018 mole) tetrabutylammonium hydrogen sulfate and the mixture is stirred at room temperature overnight. The layers are separated. The aqueous layer is extracted twice with chloroform and the combined chloroform layers are dried and evaporated to dryness. The resulting tetrabutylammonium salt is taken up in methylene chloride (20 ml) and the solution added dropwise to 20 ml of bromochloromethane at 0° C. The resulting mixture is stirred at ambient temperature for 70 hours, the solvent evaporated and ethyl acetate added to the residue. The precipitated tetrabutylammonium bromide is removed by filtration, the filtrate dried (Na₂SO₄) and evaporated in vacuo to obtain 5 g (91%) of crude product. Purification by silica gel chromatography, eluting with 1:3 ethyl ether/hexane gave 1.9 g (35%) of the desired product as an oil.

¹H—NMR (CDCl₃) ppm (delta): 1.0–2.4 (m, 10H), 5.1 (s, 2H), 5.7 (s, 2H), 7.3 (s, 5H).

B. Benzyl 1,1-dioxopenicillanoyloxymethyl trans-1,4-cyclohexanedicarboxylate A solution of 4.2 g (13.5 mmole) benzyl chloromethyl trans-1,4-cyclohexanedicarboxylate, 3.63 g (14.2 mmole) sodium 1,1-dioxopenicillanate, 1.45 g (4.5 mmole) and 100 ml acetone is heated at reflux overnight. The acetone is evaporated, ethyl acetate (100 ml) added and the solution washed with water (3 times), brine and dried over anhydrous sodium sulfate. The solvent is removed by evaporation in vacuo to afford a crude product which is purified by column chromatography on silica gel, eluting with 1:1 ethyl acetate/hexane to provide 5.3 g (78%) of purified product as an oil which is used in the next step.

¹H—NMR (CDCl₃) ppm (delta): 1.3–1.65 (m, 6H), 1.65–2.6 (m, 10H), 3.4 (d, 2H), 4.4 (s, 1H), 4.55 (t, 1H), 5.1 (s, 2H), 5.8 (q, 2H), 7.3 (s, 5H); infrared spectrum (CHCl₃) cm⁻¹: 1730, 1760, 1810.

C. To a solution of 2.5 g (4.9 mmole) of the benzyl ester provided in Part B, above, in 50 ml ethyl acetate under a nitrogen atmosphere, is added 1.5 g 10% Pd/C catalyst. The resulting mixture is hydrogenated at 1–2 atmospheres pressure for about 20 minutes. The catalyst is removed by filtration and 0.82 g (4.9 mmole) sodium 2-ethylhexanoate is added to the filtrate. After stirring for 30 minutes at room temperature the mixture is concentrated to one-third volume and three volumes of ethyl ether is added. The precipitated title compound is filtered, washed with ether and dried under nitrogen to afford 1.7 g (79% step yield).

¹H—NMR (D₂O) ppm (delta): 1.3–2.4 (m, 16H), 3.4–3.6 (m, 2H), 4.6 (s, 1H), 4.9–5.0 (m, 1H), 5.7 (q, 2H); infrared spectrum (KBr) cm⁻¹: 1565, 1760, 1810, 1780.

PREPARATION G

Crystalline 1,1-Dioxopenicillanoyloxymethyl trans-1,4-Cyclohexanecarboxylic Acid To a solution of 6.07 g (12 mmole) benzyl 1,1-dioxopenicillanoyloxymethyl trans-1,4-cyclohexanedicarboxylate in 100 ml ethyl acetate under nitrogen is added 3.2 g, 10% Pd/C catalyst. The mixture is hydrogenated for 45 minutes with shaking at 50 psi (3.52 kg/cm²). The mixture is filtered, the filtrate concentrated in vacuo to afford a residual oil which crystallizes upon standing. The product is recrystallized from ethyl acetate/hexane under a nitrogen atmosphere to obtain 2.35 g of crystalline product which appeared to contain some oil. This was taken up in ethyl acetate (100 ml) and an equivalent amount of sodium 2-ethylhexanoate is added. The precipitated sodium salt is stirred for 45 minutes, concentrated to one-third volume and ethyl ether added to complete the precipitation. The sodium salt is collected by filtration, washed with ether and dried under nitrogen. The sodium salt is taken up in water (50 ml) acidified with hydrochloric acid and the mixture extracted with ethyl acetate. The extracts are dried (Na₂SO₄), the solvent evaporated in vacuo, the residue crystallized from ethyl acetate/hexane and dried under nitrogen to obtain 1.85 g (37%) of product, m.p. 118.5°–119° C. which is found to be crystalline by X-ray diffraction.

¹H—NMR (CDCl₃) ppm (delta): 1.4 (s, 3H), 1.4–1.55 (m, 4H), 1.6 (s, 3H), 2.05–2.15 (m, 4H), 2.25–2.45 (m, 2H), 3.4–3.6 (m, 2H), 4.4 (s, 1H), 4.6–4.65 (m, 1H), 5.7–5.95 (dd, 2H); infrared spectrm (KBr) cm$^{-1}$: 1700, 1760, 1780, 1800.

PREPARATION H

A. 1,1-Dioxopenicillanoyloxymethyl glutaric acid

Benzyl 1,1-dioxopenicillanoyloxymethyl glutarate is subjected to hydrogenolysis by the method of Preparation E. After evaporation of ethyl acetate from the filtrate, the residual oil is taken up in isopropanol, the mixture stirred at 22° C. for 60 minutes and held overnight at 50° C. The resulting solid is taken up in isopropanol, filtered and washed with cold isopropanol and hexane. The resulting crystals of 1,1-dioxopenicillanoyloxymethyl glutaric acid are vacuum dried at room temperature to obtain a 63% yield, m.p. 76°–78° C.

B. 1,1-Dioxopenicillanoyloxymethyl dimethylmalonic acid

A solution of 10 g sodium 1,1-dioxopenicillanoyloxymethyl dimethylmalonate in 100 ml ethyl acetate is treated with hydrochloric acid (23 ml 1 N in 50 ml water). The mixture is stirred, then allowed to stand. The organic layer is separated, dried, the solvent evaporated in vacuo and the residue chromatographed on 400 g silica gel, eluting with 1:1 ethyl acetate/acetone. The product fractions are combined and solvent evaporated. The resulting viscous oil is dissolved in ethyl ether, filtered to remove insolubles and the filtrate is evaporated to obtain an oil which crystallizes upon scratching, 7.2 g of white crystals, m.p. 121°–123° C.

Analysis: Calculated for $C_{14}H_{19}O_9NS$: C, 44.56; H, 5.07; N, 3.71. Found: C, 44.13; H, 5.19; N, 3.65.

PREPARATION I

Tetrabutylammonium 6-[D-(2-[1-methyl-2-methoxycarbonylvinylamino]-2-[4-hydroxyphenyl]acetamido)]penicillanate To 300 ml of dichloromethane was added 41.9 g of 6-(2-amino-2-[4-hydroxyphenyl]acetamido)penicillanic acid trihydrate and 50 ml of water, and then the pH was adjusted to 8.5 using 40% aqueous tetrabutylammonium hydroxide. Three layers were obtained. The upper layer was removed, saturated with sodium sulfate and then it was extracted with dichloromethane. The extracts were combined with the middle layer and the lower layer, and the resulting mixture was evaporated in vacuo to give an oil which crystallized on trituration with acetone. This afforded 44.6 g of tetrabutylammonium 6-(2-amino-2-[4-hydroxyphenyl]acetamido)penicillanate.

The above salt was added to 150 ml of methyl acetoacetate and the suspension was heated at ca. 65° C. until a clear solution was obtained (8 minutes). The mixture was allowed to cool, and then the solid was recovered by filtration. The solid was washed with methyl acetoacetate, followed by diethyl ether, to give 49.25 g of tetrabutylammonium 6-(2-[1-methyl-2-methoxycarbonylvinylamino]-2-[4-hydroxyphenyl]acetamido)-penicillanate crystals.

PREPARATION J

Benzyl dimethylmalonate half ester

To 75 ml water containing 4.0 g sodium hydroxide is added at 0° C., 17.0 g (0.05 mole) tetrabutylammonium hydrogen sulfate, the mixture is stirred 15 minutes, allowed to warm and 100 ml chloroform containing 14.2 g (0.05 mole) dibenzyl malonate and 6.6 ml (0.10 mole) methyl iodide is added. The mixture (initial pH>12) is stirred for 30 minutes at which time the mixture is pH ca. 8. Stirring is continued for ten minutes, the organic phase is separated. To the organic layer is added another charge of 4.0 g sodium hydroxide, 17.0 g tetrabutylammonium hydrogen sulfate in 75 ml water and 6.6 g methyl iodide. The resulting mixture is stirred at room temperature for 30 minutes, the chloroform layer is separated, dried ($Na_2SO_4$) and concentrated in vacuo. The resulting residual oil is triturated with 500 ml ethyl ether, the resulting solids are filtered, washed well with ether and the filtrate and washings evaporated to afford 15.0 g (96%) of product which is identified by $^1H$—NMR spectrum as dibenzyl dimethylmalonate.

A solution of 3.12 g (48 mmole) of 85% potassium hydroxide in 75 ml benzyl alcohol is added to 15.0 g dibenzyl dimethylmalonate in 75 ml benzyl alcohol. The resulting solution is stirred for 60 hours, 1.5 liters of ethyl ether added and the resulting mixture extracted twice with 100 ml portions of water. The combined aqueous layers are washed with 100 ml ether. To the aqueous layer is added 100 ml ethyl ether and the mixture is acidified to pH 2.5 with 6 N hydrochloric acid. The ether layer is separated and the aqueous phase extracted again with ether. The ether extracts are dried ($Na_2SO_4$) and solvent evaporated to afford the product as a colorless oil, 8.6 g (81%). $R_f$ 0.1 (TLC, 2:1 hexane/ethyl acetate). Structure verified by $^1H$—NMR.

PREPARATION K

Benzyl chloromethyl adipate

To 350 ml of bromochloromethane cooled to 0° C. is added 67 g (0.14 mole) tetrabutylammonium salt of benzyl adipate half ester and the mixture is stirred overnight at 0° C. then allowed to warm to room temperature. The excess bromochloromethane is evaporated in vacuo, 400 ml ethyl ether is added to the residue and the mixture is stirred to form crystals of tetrabutylammonium bromide. The crystals are removed by filtration, washed with ether, stirred with ethyl acetate (300 ml) for one hour and refiltered and washed with ethyl acetate. The combined filtrates are evaporated in vacuo, the residue purified by chromatography on silica gel (1 kg), eluting with 2:1 hexane/ethyl acetate, to yield 19.1 g (48%) of the title compound. $^1H$—NMR ($CDCl_3$) ppm (delta): 1.58–1.9 (m, 4H), 2.2–2.62 (m, 4H), 5.13 (s, 2H), 5.68 (s, 2H), 7.38 (s, 5H).

The benzyl chloromethyl esters of the benzyl dicarboxylic acid half esters of Preparation A are prepared in like manner.

PREPARATION L

Benzyl 6-alpha-bromo-6-beta-(benzyloxycarbonylaminomethyl)penicillanate and 6-beta-bromo-6-alpha-(benzyloxycarbonylaminomethyl)penicillanate To a solution of benzyl 6,6-dibromopenicillanate (108.73 g, 0.242 mole) in 600 ml dry tetrahydrofuran (THF), cooled to −78° C., was added an ether solution of methyl magnesium bromide (83.5 ml of 2.9 M). After stirring for 15 minutes at −78° C., a solution of benzyloxycarboxamidomethyl acetate (27 g, 0.121 mole) in 200 ml dry THF was added over 10 minutes. After stirring for an hour at −78° C., the reaction was quenched by the addition of 14.52 ml of acetic acid. The mixture was warmed to room temperature and volatiles removed in vacuo at less than 35° C. Ethyl acetate was added to dissolve the residue, and the solution washed with water (100 ml), aqueous NaHCO$_3$ (100 ml), and 2×100 ml water, then dried over Na$_2$SO$_4$ and concentrated in vacuo to 113 g of oily product. The oil was column chromatographed on 1.2 kg silica gel, eluting first with 6 liters of 1:1 hexane:chloroform and then with chloroform. The first 6 liters of eluate was discarded. Further eluate was collected in 25 ml fractions. Fraction numbers 181–190 were concentrated. The pnmr spectrum of the residue in CDCl$_3$ revealed benzyl 6-alpha-bromo-6-beta-(benzyloxycarbonylaminomethyl)penicillanate: delta/TMS 1.37 (3H, s), 1.57 (3H, s), 3.86 (2H, d, J=6 Hz), 4.42 (1H, s), 5.06 (2H, s), 5.12 (2H, s), 5.52 (1H, s), 7.25 (10H, s). Fraction numbers 201–249 were concentrated and the pnmr spectrum of this residue in CDCl$_3$ revealed benzyl 6-beta-bromo-6-alpha-(benzyloxycarbonylaminomethyl)penicillanate: delta/TMS 1.36 (3H, s), 1.60 (3H, s), 3.90 (2H, d, J=6.2 Hz), 4.47 (1H, s), 5.07 (2H, s), 5.14 (2H, s), 5.40 (1H, t, J=6.2), 5.47 (1H, s), 7.28 (5H, s), 7.30 (5H, s). The product from fraction numbers 171–240 was combined and concentrated to 22 g of foam and used in the next experiment.

PREPARATION M

Benzyl 6-beta-(Benzyloxycarbonylaminomethyl)penicillanate

To a solution of title products (epimeric mixture) of Preparation L (22 g, 0.0413 mole) in 100 ml benzene was added tri-n-butyltin hydride (32.7 ml, 0.124 mole). The mixture was refluxed under N$_2$ for 2 hours, concentrated in vacuo to an oil and the oil triturated 4×100 ml hexane. The residual viscous oil was taken up in 70 ml of ether, from which title product crystallized over 1 hour [8.1 g in two crops] pnmr/CDCl$_3$/delta/TMS: 1.37 (3H, s), 1.57 (3H, s), 3.58 (3H, m), 4.34 (1H, s), 5.04 (2H, s), 5.12 (2H, s), 5.33 (1H, d, J=4 Hz), 7.32 (10H, s).

Benzyl 6-alpha-(benzyloxycarbonylaminomethyl)penicillanate is recovered by concentration of mother liquors and chromatography.

PREPARATION N

Benzyl 6-beta-(Benzyloxycarbonylaminomethyl)penicillanate 1,1-Dioxide

To a solution of title product of Preparation M (8.0 g, 0.0176 mole) in 200 ml ethyl acetate cooled to 0°–5° C. was added m-chloroperbenzoic acid (10.68 g, 0.0528 mole). The mixture was warmed to room temperature, stirred for 6 hours, recooled to 0°–5° C. and diluted with 50 ml of saturated NaHSO$_3$. The organic layer was separated, washed 2×50 ml saturated NaHCO$_3$ and 2×50 ml H$_2$O, dried over Na$_2$SO$_4$ and concentrated in vacuo to a viscous oil (8.6 g). The oil was chromatographed on 250 g silica gel, eluting with 19:1 CHCl$_3$:ethyl acetate in 25 ml fractions. Fractions 44–150 were combined and concentrated in vacuo to yield title product as a white gummy foam [7.6 g; pnmr/CDCl$_3$/delta/TMS 1.25 (3H, s), 1.49 (3H, s), 3.98 (3H, m), 4.45 (1H, s), 4.59 (1H, d, J=4 Hz), 5.09 (2H, s), 5.19 (2H, q), 5.36 (1H, br), 7.36 (10H, s)].

PREPARATION O

Benzyl 6-alpha-(Benzyloxycarbonylaminomethyl)penicillanate 1,1-Dioxide

To the title 1,1-dioxide of the preceding Preparation (3.3 g, 6.79 mmoles) in 150 ml CHCl$_3$ was added 1,5-diazabicyclo[4.3.0]non-5-ene (DBN, 0.841 g, 6.79 mmoles). The mixture was stirred at room temperature for 15 minutes, diluted with 75 ml 1 N HCl, and the layers separated. The organic layer was washed 2×50 ml H$_2$O, dried (Na$_2$SO$_4$) and concentrated in vacuo to an oil (3.1 g crude). It was purified by column chromatography on 150 g silica gel, eluting with 1:9 ethyl acetate:CHCl$_3$ in 20 ml fractions. Fractions 26–37 were combined and concentrated in vacuo to yield purified title product, as a viscous oil which crystallized on standing [1.9 g; m.p. 112°–113° C.; pnmr/CDCl$_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s)].

PREPARATION P

6-alpha-(Aminomethyl)penicillanic Acid 1,1-Dioxide

Title product of Preparation O (1.7 g), THF (40 ml), H$_2$O (40 ml) and 10% Pd/C (1.7 g) were combined and hydrogenated at 50 psig for 1 hour. Catalyst was recovered by filtration and THF removed from the filtrate in vacuo. The aqueous layer was washed with 30 ml ethyl acetate, and concentrated in vacuo to a crystalline product [0.7 g; pnmr/250 MHz/D$_2$O/DSS 1.44 (3H, s), 1.59 (3H, s), 3.63 (2H, d, J=5.5 Hz), 4.07 (1H, td, J=2, 5.5 Hz), 4.31 (1H, s), 5.06 (1H, d, J=2)].

To obtain the hydrochloride salt, the title product is dissolved in water, an equivalent of dilute hydrochloride acid is added dropwise, and the resulting solution freeze dried.

To obtain the potassium or sodium salt, the title product is dissolved in water at 0°–5° C., one equivalent of potassium or sodium hydroxide is added with vigorous stirring and the solution freeze dried.

PREPARATION Q

Iodomethyl 6-alpha-(benzyloxycarbonylaminomethyl)penicillanic Acid 1,1-Dioxide

A. 6-alpha-(Benzyloxycarbonylaminomethyl)penicillanic acid 1,1-dioxide 6-alpha-(Aminomethyl)penicillanic acid 1,1-dioxide (2.62 g, 0.01 mole) is added to 20 ml water and 80 ml acetone at 15°–20° C., and the pH adjusted to 8 with dilute NaOH. A solution of benzyl chloroformate (1.88 g, 0.011 mole) in 20 ml acetone is added dropwise at 15°–20° C. while simultaneously maintaining the apparent pH of the reaction between 7 and 8 by the periodic addition of dilute NaOH. The reaction mixture is allowed to stir for 30 minutes, and is then concentrated in vacuo to remove most of the acetone. The aqueous solution is extracted twice with ethyl acetate and the extracts discarded. Fresh ethyl acetate (100 ml) is added to the water layer and the pH adjusted to 2 with dilute hydrochloric acid, with stirring. The organic layer is removed, washed with brine, dried over Na$_2$SO$_4$, and concentrated in vacuo to provide the title product.

B. Chloromethyl 6-alpha-(benzyloxycarbonylaminomethyl)penicillanate 1,1-dioxide The product of Part A, above, (1 g) is combined with 10 ml of methylene chloride and 2 ml of water and the pH adjusted to 8.0 with 40% tetrabutylammonium hydroxide over a period of 15 minutes. The methylene chloride layer is separated and the aqueous layer extracted with three 2 ml portions of fresh methylene chloride. The methylene chloride layers are combined, dried over $Na_2SO_4$, and concentrated in vacuo to yield tetrabutylammonium salt. The salt is combined with 10 ml of chloroiodomethane, the mixture stirred for 16 hours, and concentrated to dryness in vacuo to yield the desired ester.

C. The chloromethyl ester obtained in above (0.24 g) is combined with 3 ml of acetone and sodium iodide (0.58 g) and the mixture stirred for 16 hours. The reaction mixture is concentrated in vacuo and the residue distributed between 7.5 ml of ethyl acetate and 5.0 ml of water. The ethyl acetate is separated, washed in sequence with two 25 ml portions of water and one 25 ml portion of brine, dried over $Na_2SO_4$ and concentrated in vacuo to provide the title product.

PREPARATION R 1,1-Dioxo-6-alpha-(aminomethyl)penicillanoyloxymethyl Adipic Acid, Sodium Salt A. Employing benzyl adipate half ester and iodomethyl 6-alpha-(benzyloxycarbonylaminomethyl)-penicillanate 1,1-dioxide as reactants in the procedure of Preparation C affords benzyl 1,1-dioxo-6-alpha-(benzyloxycarbonylaminomethyl)penicillanoyloxymethyl adipate.

B. Hydrogenolysis and reaction of the resulting carboxylic acid with sodium-2-ethylhexanoate (Preparation D) provides the title sodium salt. Use of potassium 2-ethylhexanoate affords the corresponding potassium salt.

PREPARATION S

Chloromethyl Penicillanate 1,1-Dioxide

A mixture of 4.66 g of penicillanic acid 1,1-dioxide, 50 ml of dichloromethane and 35 ml of water was treated with sufficient tetrabutylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetrabutylammonium salt of penicillanic acid 1,1-dioxide.

The above tetrabutylammonium penicillanate 1,1-dioxide was added to 50 ml of chloroiodomethane and the reaction mixture allowed to stir at ambient temperature overnight. The reaction mixture was concentrated to half volume in vacuo, and chromatographed on 200 g of silica gel using ethyl acetate/hexane as the eluant, 12 ml cuts being taken every 30 sec. Fractions 41–73 were combined and concentrated to dryness to give 3.2 g of the title compound.

The NMR spectrum ($CDCl_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION T

Iodomethyl Penicillanate 1,1-Dioxide

To a solution of 7.9 g of chloromethyl penicillanate 1,1-dioxide in 100 ml of dry acetone maintained under a nitrogen atmosphere was added 21.0 g of sodium iodide, and the reaction mixture was allowed to stir overnight at room temperature. The reaction mixture was concentrated in vacuo, and the residue was dissolved in 150 ml ethyl acetate and 150 ml water. The organic layer was separated and the aqueous layer was extracted with fresh ethyl acetate. The organic extracts were combined, washed with water (1×500 ml) and brine (1×50 ml) and dried over sodium sulfate. Removal of the solvent gave 10.5 g of the title product, m.p. 100°–102° C.

The NMR spectrum ($CDCl_3$) showed absorptions at 1.55 (s, 3H), 1.68 (s, 3H), 3.5 (d, 2H), 4.4 (s, 1H), 4.65 (t, 1H) and 6.0 (dd, 2H) ppm.

Similarly, following the procedures of Preparations S and T, the iodomethyl derivative of 6-beta-hydroxymethylpenicillanate 1,1-dioxide is produced from 6-beta-hydroxymethylpenicillanate 1,1-dioxide.

I claim:

1. A compound having the formula

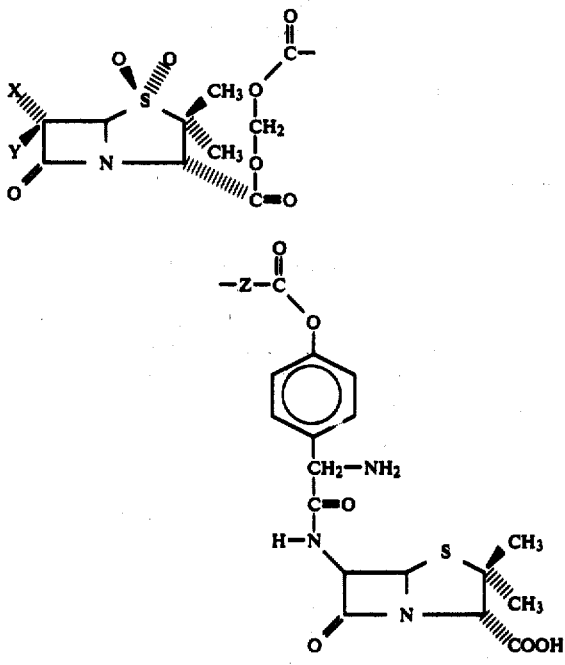

wherein

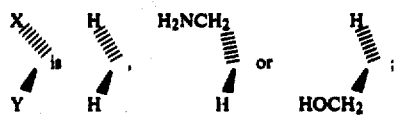

and Z is 1,4-cyclohexylene or alkylene having from 1 to 6 carbon atoms;

or a pharmaceutically acceptable salt thereof.

2. A compound according to claim 1 wherein

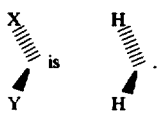

3. The compound according to claim 2 wherein Z is trans-1,4-cyclohexylene.

4. A compound according to claim 2 wherein Z is alkylene having from 3 to 4 carbon atoms.

5. The compound according to claim 4 wherein Z is —(CH$_2$)$_4$—.

6. A compound according to claim 1 wherein

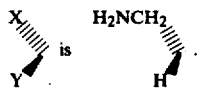

7. The compound according to claim 6 wherein Z is trans-1,4-cyclohexylene.

8. The compound according to claim 6 wherein Z is —(CH$_2$)$_3$.

9. The compound according to claim 1 wherein

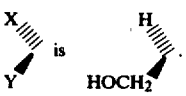

10. The compound according to claim 9 wherein Z is trans-1,4-cyclohexylene.

11. The compound according to claim 9 wherein Z is —(CH$_2$)$_3$.

12. A method of treating a bacterial infection in a mammalian subject in need of such treatment, which comprises administering thereto an antibacterially effective amount of a compound according to claim 1.

13. A pharmaceutical composition suitable for treating a bacterial infection in a mammalian subject, which comprises an antibacterially effective amount of a compound according to claim 1 and a pharmaceutically acceptable carrier.

* * * * *